United States Patent
Modrak

(10) Patent No.: US 6,541,462 B1
(45) Date of Patent: Apr. 1, 2003

(54) SPHINGOMYELIN ENHANCEMENT OF TUMOR THERAPY

(75) Inventor: David Modrak, Nutley, NJ (US)

(73) Assignee: Center for Molecular Medicine and Immunology, Belleville, NJ (US)

( * ) Notice: Subject to any disclaimer, the term of this patent is extended or adjusted under 35 U.S.C. 154(b) by 0 days.

(21) Appl. No.: 09/533,799

(22) Filed: Mar. 24, 2000

Related U.S. Application Data

(60) Provisional application No. 60/126,189, filed on Mar. 25, 1999.

(51) Int. Cl.[7] .................. A01N 57/26; A01N 43/04; A61K 51/00
(52) U.S. Cl. .................. 514/78; 514/25; 514/33; 514/34; 514/76; 424/1.49; 424/1.11
(58) Field of Search .................. 424/450, 174.1, 424/181.1, 1.49, 1.11; 514/25, 33, 34, 274, 50, 76, 78; 536/6.4

(56) References Cited

U.S. PATENT DOCUMENTS

| | | | |
|---|---|---|---|
| 5,543,152 A | * 8/1996 | Webb et al. | 424/450 |
| 5,631,394 A | 5/1997 | Wei et al. | 556/404 |
| 5,677,337 A | 10/1997 | Wei et al. | 514/546 |
| 5,681,589 A | 10/1997 | Wei et al. | 424/450 |
| 5,785,987 A | * 7/1998 | Hope et al. | 424/450 |

OTHER PUBLICATIONS

"Sphingomyelin potentiation of chemotherapy in HT–29 bearing nude mice,", *Proceedings of the American Association For Cancer Research Annual Meeting, 90th Annual Meeting of the American Association for Cancer Research*, Philadelphia, PA, (Apr. 1999).

"Characterization of 5–fluorouracil loaded liposomes prepared by reverse–phase evaporation or freezing–thawing extrusion methods: Study of drug release," *Biochimica et Biophysica Acta, 1153* (2):135–142, (1993).

"$Ca^{2+}$ transport inhibition by the antitumor agents adriamycin and daunomycin," *Arzneimittel–Forschung/Drug Research* 27(6):1177–1180, (1977).

"Loading or doxorubicin into liposomes by forming $Mn^{2+}$ –drug complexes," *Biochimica et Biophysica Acta*, 1414:205–216 (1998).

Kinya Koizumi et al., "Rapid Isolation and Lipid Characterization of Plasma Membranes From Normal and Malignant Lymphoid Cells of Mouse," *Biochimica et Biophysica Acta*, 649:393–403 (1981).

Wim J. Van Blitterswijk et al., "Differences In Membrane Lipid Composition and Fluidity of Trannsplanted GRSL Lymphoma Cells, Depending on Their Site of Growth in the Mouse," *Biochimica et Biophysica Acta*, 778:521–529 (1984).

Ali Bettaieb et al., "Opposite Effects of Tumor Necrosis Factor α on the Sphingomyelin–Ceramide Pathway in Two Myeloid Leukemia Cell Lines: Role of Transverse Sphingomyelin Distribution in the Plasma Membrane," *Blood*, 88:1465–1472 (1996).

* cited by examiner

*Primary Examiner*—Michael G. Hartley
(74) *Attorney, Agent, or Firm*—Foley & Lardner

(57) ABSTRACT

Cytotoxic tumor therapy in a patient is enhanced by co-administration of sphingomyelin. The invention most likely enhances a tumor cell's ability to undergo ceramide-induced apoptosis by increasing the levels of sphingomyelin in all cellular compartments, thereby providing sufficient substrate for activated sphingomyelinase. A method of treating rheumatoid arthritis also is provided.

10 Claims, 4 Drawing Sheets

US 6,541,462 B1

SPHINGOMYELIN ENHANCEMENT OF TUMOR THERAPY

This application is based on U.S. Provisional Application Serial No. 60/126,189, filed on Mar. 25, 1999.

GOVERNMENT LICENSE RIGHTS

The U.S. Government has a paid-up license in this invention and the right in limited circumstances to require the patent owner to license others on reasonable terms as provided for by the terms of grant number CA 54425-07, awarded by the National Institutes of Health.

BACKGROUND OF THE INVENTION

Traditionally, the efficacy of many cancer therapies was believed to arise from the cytotoxicity derived from chemotherapy- or radiation-induced DNA damage. Such DNA damage was considered to trigger an apoptotic response. See Eastman et al., Cancer Invest., 10: 229–240 (1992); Allan, D. J., Int. J. Radiat. Biol., 62: 145–152 (1992). Apoptosis is conceptualized as an inducible preprogrammed pathway of sequential biochemical events, leading to activation of calcium- and magnesium-dependent endonucleases that cleave the nuclear chromatin at selective internucleosomal linker sites. Signals generated at the membrane of the affected cell activate neighboring cells and infiltrating macrophages to phagocytize the dying cell and its disintegrating nucleus.

An early hypothesis on the nature of the lethal damage produced by ionizing radiation identified heterologous double strand breaks in the DNA as the most common type of lesions that lead to mammalian cell death. See Radford, I. R., Int. J. Radiat. Biol., 49: 611–620 (1986); Ward, J. F., Prog. Nucleic Acid Mol. Biol., 35: 95–125 (1988). Such lesions are produced in the DNA by direct interaction with X-rays, or with reactive oxygen intermediates generated within the cell by the radiation. See Steel et al., Int. J. Radiat. Biol., 56: 525–537 (1989). While mammalian cells are proficient in repairing most DNA double strand breaks, not all such lesions are repairable. See Ward, J. F., Prog. Nucleic Acid Mol. Biol., 35: 95–125 (1988). Residual unrepaired DNA lesions can lead to post-mitotic cell death. See Bedford, J. S., Int. J. Radiat. Oncol. Biol. Phys., 21: 1457–1469 (1991). Therefore, until recently, inefficiency of DNA repair was thought to play a key role in radiation sensitivity.

Similarly, some chemotherapies, for example anthracycline daunorubicin (DNR), were believed to induce cytotoxicity as a result of drug-induced damage to DNA. It was suggested that damage to genetic material could result from free radicals stemming from the quinone-generated redox activity, from intercalation-induced distortion of the double helix, or from stabilization of the cleavable complexes formed between DNA and topoisomerase II. See Chabner et al., Cancer: Principles and Practice of Oncology, J.B. Lippencott Co., Philadelphia, Pa. Pp 349–395 (1989). However, the mechanism by which such damage induced the apoptotic pathway remained unclear.

In recent years, an alternative to the hypothesis that direct DNA damage from cancer therapies mediates induced apoptosis has been established. The sphingomyelin signal transduction pathway for induction of apoptosis has emerged as a leading mechanism in many cancer therapies, including ionizing radiation, tumor necrosis factor α (TNF-α) and daunorubicin. See Haimovitz-Friedman et al., J. Exp. Med., 180: 525–535 (1994); Kolesnick et al., Cell, 77: 325–328 (1994); Jaffrezou et al., Embo J., 15: 2417–2424 (1996); Bose et al., Cell, 82: 405–414 (1995).

Sphingomyelin is a class of sphingolipids, which constitute a major lipid class in the cell, especially the plasma membrane. See Merrill et al., Toxicol. Appl. Pharmcol., 142: 208–225 (1997). Sphingomyelin is compartmentalized into two distinct pools in the plasma membrane. See Linardic et al., J. Biol. Chem., 269: 23530–23537 (1994). It has been proposed that the sphingomyelin pool localized to the inner leaflet of the plasma membrane is dedicated exclusively to intracellular signaling. The observation that there is no difference in sphingomyelin molecular species between the two pools of sphingomyelin in the plasma membrane suggests the importance of compartmentalization in signal transduction. See Fritzgerald et al., Lipids, 30: 805–809 (1995).

Many cancer therapies initiate the sphingomyelin pathway by inducing the rapid hydrolysis of sphingomyelin to ceramide. Ceramide plays a pivotal role in a variety of cellular processes, including regulating programmed cell death. See Merrill et al., Toxicol. Appl. Pharmcol., 142: 208–225 (1997). The specificity of ceramide as a second messenger for apoptosis was demonstrated by the fact that cell-permeable ceramide analogs, but not analogs of other lipid second messengers, were able to recapitulate the effects of TNF-α, Fas, and ionizing radiation and induce apoptosis directly. Induction of apoptosis by ceramide is also stereospecific, since dihydroceramide fails to induce apoptosis. It has been proposed that ceramide initiates apoptosis by activating the stress-activated protein kinase pathway. See Verheij et al., Nature, 380: 75–79 (1996).

While many therapies are successful in initiating the sphingomyelin transduction pathway, the induced apoptotic response may be limited or short-lived. For unknown reasons, tumor cells have abnormal lipid composition, including sphingomyelin. Tumor tissues typically have higher concentrations of sphingomyelin than normal tissues; however, it is possible that some tumor cells have reduced sphingomyelin synthesis capabilities. See Koizumi et al., Biochim. Biophys. Acta., 649: 393–403 (1991); Van Blitterswijk et al., Biochim. Biophys. Acta., 778: 521–529 (1984). Additionally, altered lipid metabolism in tumor cells can result in changes in the intracellular distribution of sphingomyelin. Such redistribution within the plasma membrane can lead to misdirected sphingomyelin which is unable to be acted upon by the sphingomyelin hydrolyzing enzymes responsible for generating ceramide in response to cytotoxic treatment. See Bettaieb et al., Blood, 88: 1465–1472 (1996). Consequently, sphingomyelin re-organization within the plasma membrane can impair a tumor cell's ability to generate ceramide-induced apoptosis and lead to reduced sensitivity to certain therapies.

A need, therefore, continues to exist for a method for overcoming tumor cell alteration of lipid metabolism in order to maximize a tumor therapy utilizing the sphingomyelin pathway for induction of apoptosis.

SUMMARY OF THE INVENTION

It is, therefore, one object of the present invention to provide a method of enhancing tumor therapies utilizing the sphingomyelin pathway for induction of apoptosis.

It is also an object of the present invention to provide a method of treating rheumatoid arthritis.

In accomplishing these and other objects of the invention, there is provided, in accordance with one aspect of the present invention, a method of enhancing cytotoxic tumor therapy in a mammalian patient, comprising administering to the patient in conjunction with the therapy, a therapeutically effective amount of sphingomyelin. In preferred embodiments of the present invention, the above method may be used for enhancing tumor therapy selected from one or more of the following: chemotherapy, ionizing radiation, immunotherapy and radioimmunotherapy.

In one embodiment of the present invention, naturally occurring sphingomyelin (C16:0) is administered along with tumor therapy. In another embodiment, sphingomyelin molecules with shorter side chains ($C_2$–$C_{15}$) are utilized.

In yet another embodiment of the present invention, sphingomyelin is administered to a patient orally, while in another embodiment it is administered parenterally.

In accordance with another aspect of the present invention, there is provided a method of treating rheumatoid arthritis in a mammalian patient, comprising administering to the patient an amount of sphingomyelin effective to increase ceramide production and resultant apoptosis in proliferating synovial fibroblasts.

In another embodiment, there is provided a pharmaceutical composition comprising an amount of sphingomyelin effective to enhance apoptosis in a mammalian patient, for use in conjunction with cytotoxic tumor therapy. There is provided also a pharmaceutical composition comprising an amount of sphingomyelin effective to increase ceramide production and resultant apoptosis in proliferating synovial fibroblasts in mammals.

In other embodiments, there are provided kits useful for enhancing cytotoxic tumor therapy and for treating rheumatoid arthritis, comprising sphingomyelin and ancillary reagents to effect administration of the sphingomyelin.

Other objects, features and advantages of the present invention will become apparent from the following detailed description. It should be understood that examples are given by way of illustration only, since various changes and modifications within the spirit and scope of the invention will become apparent to those skilled in the art.

DETAILED DESCRIPTION

Figure 1:
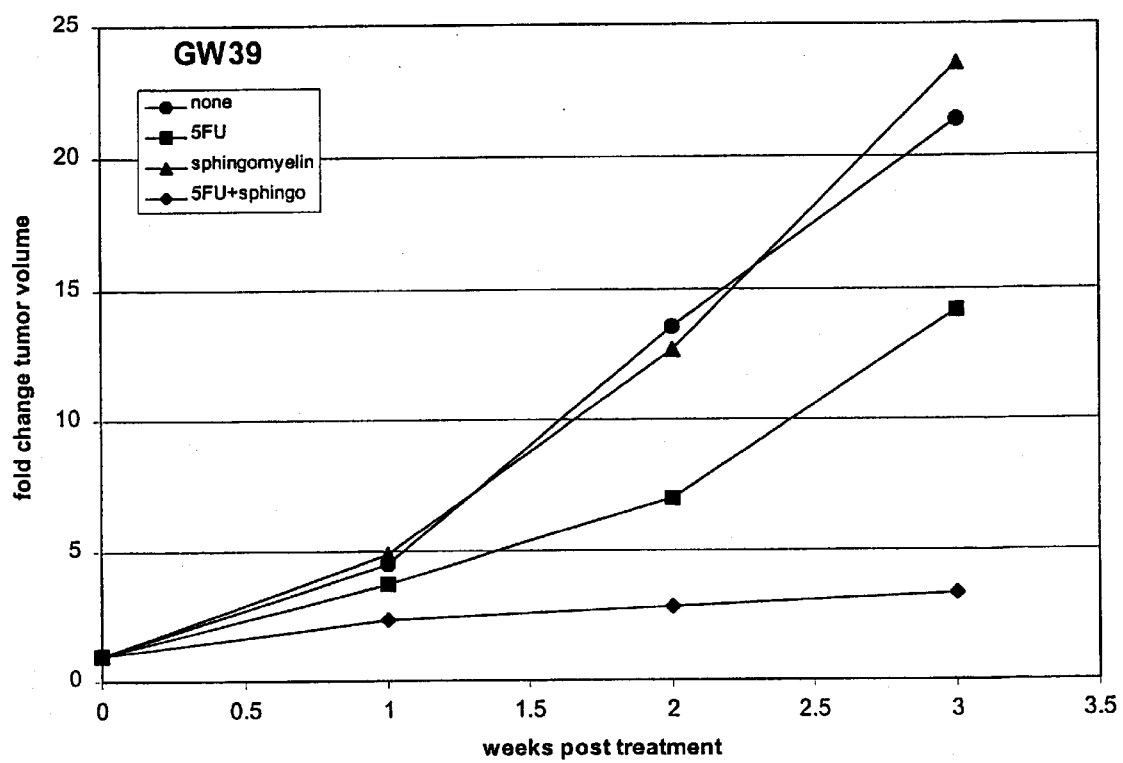
FIG. 1 demonstrates graphically that co-administration of 5-flurouracil and sphingomyelin reduces the rate of GW39 tumor growth to a much greater degree and for a longer time than 5-fluorouracil alone.

The present invention enhances tumor therapy. The invention is believed to enhance a tumor cell's ability to undergo ceramide-induced apoptosis by increasing the levels of sphingomyelin in all cellular compartments, thereby providing sufficient substrate for activated sphingomyelinase. Tumor cells typically have altered lipid metabolism, including abnormal sphingomyelin composition and compartmentalization. Most studies suggest that tumor tissues have increased concentrations of sphingomyelin. While most tumor cells may have abnormally high levels of sphingomyelin, it may be unavailable to its hydrolyzing enzyme, sphingomyelinase, due to abnormal, subcellular compartmentalization of sphingomyelin. The alteration of sphingomyelin metabolism can impair a tumor cell's ability to generate ceramide and can lead to reduced sensitivity to certain therapies. Surprisingly and unexpectedly, the present invention demonstrates that administration of additional sphingomyelin increases the tumoricidal activity of tumor therapy.

In accordance with one aspect of the present invention, the tumoricidal activity of tumor therapy is increased by administering to the patient a therapeutically effective amount of sphingomyelin along with the therapy. While the invention is not limited to the proposed mechanism, the administration of sphingomyelin is likely to enhance any therapy which utilizes the sphingomyelin signal transduction pathway for induction of apoptosis. This includes, but is not limited to, therapies which seek to control or inhibit rapid, abnormal growth. Examples include, but are not limited to, tumor therapies, such as chemotherapy, ionizing radiation, immunotherapy and radioimmunotherapy, and cell-mediated therapy of viral infection.

In a preferred embodiment of the present invention, a therapeutically effective amount of sphingomyelin is administered to a patient undergoing tumor therapy with chemotherapy. Sphingomyelin can be co-administered with a variety of chemotherapies. Examples include, but are not limited to, epipodophyllotoxins (e.g., etoposide, tenoposide) anthracyclines (e.g., doxorubicin/adriamycin, daunorubicin, idarubicin), Vinca alkoloids (e.g., vincristine, vinblastine), camptothecins, taxanes (e.g., Taxol) and metabolic inhibitors (e.g., 5FU, gemcitabine).

In a further embodiment, the chemotherapy may be targeted to the tumor cells using an antibody or antibody fragment. Use of antibodies, antibody fragments, or receptor binding peptides to specifically target tumor cells increases the delivery of tumoricidal doses of chemotherapy while causing a significant reduction of toxicity to normal tissues.

In another preferred embodiment of the present invention, a therapeutically effective amount of sphingomyelin is administered to a patient undergoing tumor treatment with ionizing radiation. A variety of sources may be used to generate ionizing radiation for the purpose of tumor therapy. Examples include, but are not limited to, external beam radiation and surgical implantation of radioactive particles or strings of particles.

In still another preferred embodiment of the present invention, a therapeutically effective amount of sphingomyelin is administered to a patient undergoing tumor therapy with immunotherapy. Such treatment, utilizing unconjugated antibodies and antibody fragments, effectively induces cells to undergo apoptosis by cross-linking selected surface receptors, for example the TNF receptor.

In yet another preferred embodiment of the present invention, a therapeutically effective amount of sphingomyelin is administered to a patient undergoing tumor treatment with radioimmunotherapy. Radioimmunotherapy is an attractive therapeutic concept which offers advantages over more traditional forms of cancer treatment. The strategy seeks to deliver tumoricidal doses of radiation to tumor cells with reduced radiation toxicity to normal tissues. Radioimmunotherapy utilizes antibodies, antibody fragments, or receptor binding peptides to specifically target tumor cells. The antibodies, etc., are conjugated to radioisotopes which ideally provide sufficient irradiation to kill tumor cells. Such radiolabeled antibodies, as well as receptor-binding peptides (e.g., somatostatin analogs) have been shown to target cancer cells in animal models and in humans. See Goldenberg, D. M. (editor), *Cancer imaging with radiolabeled antibodies*. Kluwer Academic Publishers, Boston (1990); Goldenberg, D. M. (editor), *Cancer Therapy with Radiolabeled Antibodies*. CRC Press: Boca Raton (1995); Krenning et al., *J. Nucl. Med.*, 33: 652–658 (1992). As discussed above, ionizing radiation can initiate apoptosis using the sphingomyelin transduction pathway. Therefore, administering sphingomyelin with radioimmunotherapy will increase the efficacy of such treatment.

The tumoricidal activity of a variety of tumor therapies can be increased by co-administering to the patient a therapeutically effective amount of sphingomyelin along with the therapy. Examples of such therapies include, but are not limited to, oxygen radicals (e.g., $O_2$, NO), cytokines (e.g., FAS, TNFα, TRAIL), protein phosphatase inhibitors (e.g., okadaic acid), retinoids (e.g., fenretinide), steroids (e.g., β-Sitosterol), dimethylsphingosine, Δ9-Tetrahydrocannabinol, suramin, sodium butyrate, platinum compounds (e.g., cis-platin, carboplatin), immunomodulators (e.g., cyclosporin, FK506), toxins (e.g., higa-, vero-, Pseudomonas endo-) and phthalocyanine 4-photodynamic therapy. Sphingomyelin also can be used in conjunction with multidrug resistance modulators which increase ceramide levels and potentiate apoptosis (e.g., SDZ PSC 833, VX710).

In another embodiment of the present invention, a therapeutically effective amount of sphingomyelin is administered to a patient suffering from rheumatoid arthritis. The disease is characterized by a proliferation of synovial cells and an infiltration of inflammatory cells that leads to cartilage and bone destruction. Abnormal events within the apoptotic process can result in the proliferation of rheumatoid synovial fibroblasts. C2-ceramide has been shown to induce apoptosis in rheumatoid synovial fibroblasts in vitro and in vivo. See Ichinose et al., *J. Lab. Clin. Med.*, 131: 410–416 (1998). Administration of sphingomyelin is believed to increase ceramide production and, therefore, can provide an effective treatment for rheumatoid arthritis by promoting apoptosis in proliferating synovial fibroblasts. Similarly, sphingomyelin administration can effectively treat other autoimmune diseases which result from ineffective utilization of the sphingomyelin signal transduction pathway for induction of apoptosis.

In one embodiment of the present invention, naturally occurring sphingomyelin is administered to a patient to enhance the tumoricidal activity of tumor therapy. Naturally occurring sphingomyelin typically contains long, side chain derivatives ($C_{16}$–$C_{30}$ N-acyl groups). Such sphingomyelin can be obtained from commercial sources and is usually derived from egg yolk and contains primarily palmitoyl chains. See Sigma Chemicals (St. Louis, Mo.), Catalog #S0756.

The de novo biosynthesis of sphingomyelin is initiated by the condensation of serine and palmitoyl-CoA resulting in the formation of 3-ketosphinganine (3-ketodihydrosphingosine), which is subsequently reduced to dihydrosphingosine. See Hannun, Y. A., *J. Biol. Chem.*, 269: 3125–3218 (1994). Dihydroceramide is formed by the amide linkage of fatty acyl groups to dihydrosphingosine. Ceramide is formed from dihydroceramide by the introduction of the trans-4,5-double bond and serves as a precursor for all other complex sphingolipids. Sphingomyelin is formed by the addition of a phosphorylcholine head group to ceramide primarily through the transfer of choline phosphate from phosphatidylcholine through the action of phosphatidylcholine:ceramide choline phosphotransferase.

In another embodiment of the present invention, sphingomyelin with modified side chains can be administered to a patient to enhance the tumoricidal activity of tumor therapy. For example, sphingomyelin analogs with shorter-than-normal side chains, including $C_2$–$C_{15}$ side chains, can be utilized. Apoptotic studies have shown that ceramide analogs with short side chains ($C_2$, $C_8$) effectively induce apoptosis and may act more rapidly than normal length molecules. See Bose et al., *Cell*, 82: 405–414 (1995); Haimovitz-Friedman et al., *J. Exp. Med.*, 180: 525–535 (1994). Similarly, sphingomyelin analogs with shorter-than-normal side chains offer a further enhancement of the tumoricidal activity of tumor therapy agents. Alternatively, longer-than-normal side chains, including $C_{24}$, also can be effective.

Numerous strategies are well-known in the art for altering the activity of biological molecules by modifying their structure. In general, modifications to a naturally occurring compound can increase its biological activity or facilitate its uptake by appropriate cell machinery. Besides varying the length of a molecule's side chains, incorporating additional elements or functional groups also can enhance the performance of a naturally occurring compound. Examples of such substituents include, but are not limited to, aliphatic groups, e.g., $C_1$–$C_6$ straight or branched chain alkyl or cycloalkyl groups, aromatic groups, functional groups, e.g., cyano-, nitro-, azido-, halo- and epoxy- groups, and other elements, e.g., sulfur, selenium, boron and metals, as well as insertion of, e.g., oxygen or nitrogen atoms in the side chains. Sphingomyelin activity also can be enhanced by adding double or triple bonds to the molecule. See Kishida et al., *J. Lipid Mediat. Cell Signal*, 16: 127–137 (1997).

In one embodiment of the present invention, sphingomyelin is administered to a patient orally. In another embodiment, it is administered parenterally. Parenteral administration refers to a variety of methods of administrating a compound to a patient including, but not limited to, admninistration intravenously/intra-arterially, intrathecally, subcutaneously and via a transdermal patch.

In another embodiment, gene therapy is used to increase the sphingomyelin concentration within target cells of a patient undergoing cytotoxic tumor therapy. Gene therapy requires a system for introducing a vector containing an enzyme involved in the synthesis of sphingomyelin into target cells. Any enzyme, including those of mammalian, bacterial or fungal origin, which increases the concentration of sphingomyelin in a cell can be used. Examples include, but are not limited to, serinepalmitoyltransferase, ceramide synthase and sphingomyelinase.

The construction of a suitable vector can be achieved by any of the methods well-known in the art for the insertion of exogenous DNA into a vector. See Sambrook et al., 1989, *Molecular Cloning, A Laboratory Manual*, Cold Spring Harbor Press, N.Y. In addition, the prior art teaches various methods of introducing exogenous genes into cells in vivo. See Rosenberg et al., *Science* 242:1575–1578 (1988); Wolff et al., *PNAS* 86:9011–9014 (1989). The routes of delivery include systemic administration and administration in situ. Well-known techniques include systemic administration with cationic liposomes, and administration in situ with viral vectors. See Caplen et at., *Nature Med.*, 1:39–46 (1995); Zhu et al., *Science*, 261:209–211 (1993); Berkner et al., *Biotechniques*, 6:616–629 (1988); Trapnell et al., *Advanced Drug Delivery Rev.*, 12:185–199 (1993); Hodgson et al., *BioTechnology* 13: 222 (1995). Vectors and gene delivery systems which specifically direct the exogenous genes to target cells are most preferred. It is anticipated that future developments in targeted gene delivery will increase the significance of this embodiment.

A "therapeutically effective" amount of sphingomyelin can be determined by prevention or amelioration of adverse conditions or symptoms of diseases, injuries or disorders being treated. Optimization of the timing and dosage of sphingomyelin administered to a patient in conjunction with tumor therapy by convention is adapted to, among other things, the particular characteristics of the patient and the extent of the tumorgenesis. Such adaptations are routine and do not require undue experimentation or skill in the art. Similarly, optimization of the timing and dosage of sphingomyelin administered to a patient as a therapy for rheumatoid arthritis also is adapted to, among other things, the particular characteristics of the patient. The methods and pharmaceutical compositions of the invention can be used to treat a variety of mammals and are used most preferably to treat humans and domesticated animals, such as livestock and pets.

The liposomes of the invention can be combined with inert pharmaceutical excipients such as lactose, oil, mannitol and starch to form pharmaceutical compositions/ preparations. Such compositions can be formulated into dosage forms such as elixirs, liquids, ointments, lotions, IV fluids, alcohol, tablets, capsules, and the like. For parenteral, intramuscular, subcutaneous and intravenous administration, the liposomes can be formulated with an inert, parenterally acceptable vehicle such as water, saline, sesame oil, ethanol buffered aqueous medium, propylene glycol and the like. For topical and oral administration, the liposomes can be formulated with waxes, oils, buffered aqueous medium, and the like. These various pharmaceutical dosage forms are prepared by methods well-known to the pharmacist's art.

In another embodiment, there is provided a kit useful for enhancing cytotoxic tumor therapy, comprising sphingomyelin and ancillary reagents to effect administration of the sphingomyelin. Examples of ancillary reagents include, but are not limited to, buffered solutions and application devices, such as syringes. Similarly, there is provided a kit useful for treating rheumatoid arthritis in a patient, comprising sphingomyelin and ancillary reagents to effect administration of the sphingomyelin.

I. PREPARATION OF REAGENT

Preparation of Sphinyomyelin

Various forms of sphingomyelin can be obtained in powder form from Sigma Chemicals (St. Louis, Mo.). Mix 1 g of sphingomyelin powder with 9.5 ml of sterile saline or phosphate buffered saline (PBS) and QS to 10 ml. Sonicate the resulting suspension in a water bath at 80–90° C. for 1 hour. The suspension should be administered within one hour of sonication and should be approximately room temperature (25–30° C.). The suspension can be stored at 4° C.; however, it should be re-sonicated for 30 minutes in a water bath at 80–90° C. before administration.

Alternatively, liposomes of the present invention can be prepared using an extruding machine. Such machines are available from a variety of sources, e.g., AmiKa Corporation, Columbia, Md. These machines produce small, unilaminar vesicles/liposomes of defined size.

II. METHOD OF ENHANCING TUMOR THERAPY

EXAMPLE 1

In vivo Evaluation of Sphingomyelin Therapy on GW39 Colonic Tumors

Sphingomyelin enhancement of chemotherapy was evaluated by measuring its effect on 5-fluorouracil (5FU) treatment of GW39 colonic tumors in mice. Nude mice were implanted subcutaneously with GW39 tumors. After the tumors reached approximately 0.5 cm$^3$, the mice were split into groups of ten and administered one of the following therapies: no treatment (●), 0.45 mg/day of 5-fluorouracil for five days (■), 10 mg/day of sphingomyelin (SM) for seven days (▲), or 0.45 mg/day of 5-fluorouracil for five days and 10 mg/day of sphingomyelin for seven days (♦). Both the 5-fluorouracil and the sphingomyelin were administered by intravenous injection. The group receiving both 5-fluorouracil and sphingomyelin was administered both therapies for five days and then continued to receive injections of sphingomyelin for 2 days. The tumor volume in each animal was assessed at weekly intervals for three weeks following treatment.

The results are depicted graphically in FIG. 1. Sphingomyelin alone had no effect on tumor growth. Treatment with 5-fluorouracil initially slowed the rate of tumor growth, but the rate of growth increased after the second week. However, co-administration of both 5-fluorouracil and sphingomyelin reduced the rate of tumor growth to a much greater degree and for a longer time than 5-fluorouracil alone.

EXAMPLE 2

In vivo Evaluation of Sphineomyelin Therapy on HT29 Colonic Tumors

Sphingomyelin enhancement of chemotherapy was evaluated by measuring its effect on 5-fluorouracil treatment of HT29 colonic tumors in mice. Nude mice were implanted subcutaneously with HT29 tumors. After the tumors reached approximately 0.5 cm$^3$, the mice were split into groups of ten and administered one of the following therapies: no treatment (●), 0.45 mg/day of 5-fluorouracil for five days (■), 10 mg/day of sphingomyelin for seven days (▲), or 0.45 mg/day of 5-fluorouracil for five days and 10 mg/day of sphingomyelin for seven days (♦). Both the 5-fluorouracil and the sphingo-myelin were administered by intravenous injection. The group receiving both 5-fluorouracil and sphingomyelin was administered both therapies for five days and then continued to receive injections of sphingomyelin for 2 days. The tumor volume in each animal was assessed at weekly intervals for five weeks following treatment, except for the sphingomyelin only group, which was evaluated for four weeks. Averaged data from each group were fitted to an exponential growth curve using non-linear regression. The curves were compared using ANOVA.

Figure 2:
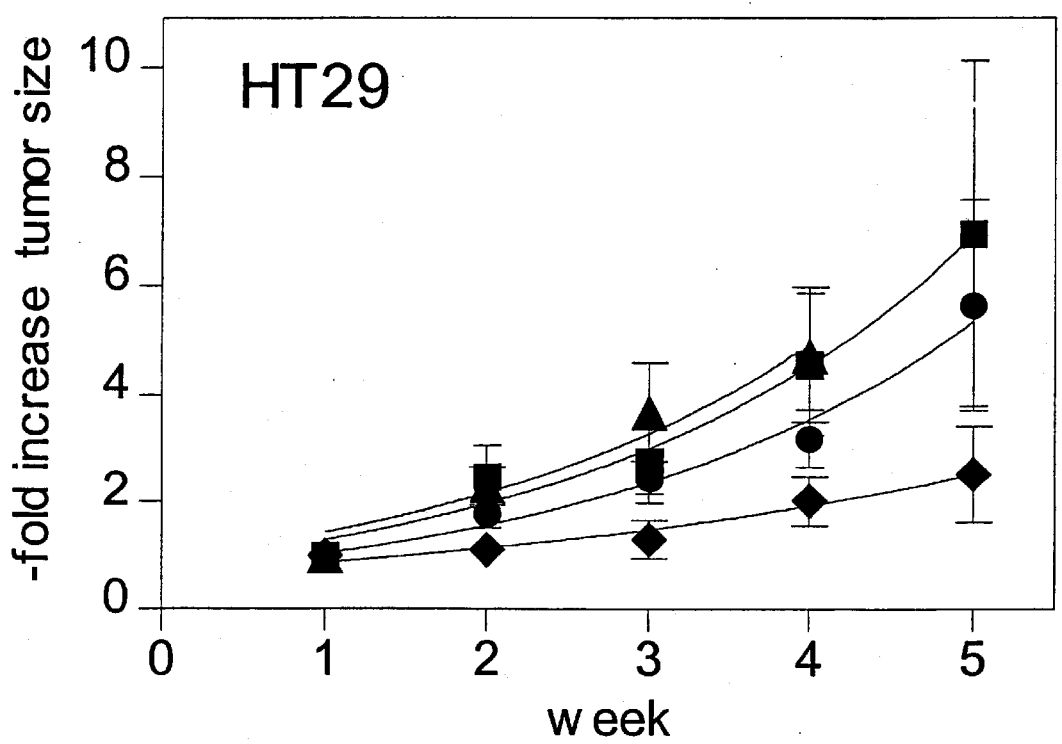
FIG. 2 shows graphically that co-administration of sphingomyelin enhances 5-flurouracil treatment of HT29 tumors. The test groups were as follows: no treatment (●), 0.45 mg 5FU/day for 5 days (■), 10 mg SM/day for 7 days (▲) or the combination of 5FU and SM initiated on the same day (◆).

The results are depicted graphically in FIG. 2. Neither sphingomyelin nor 5-fluorouracil, administered alone, had an effect on tumor growth (p>0.1 for each compound compared to no treatment group). However, co-administration of both 5-fluorouracil and sphingomyelin reduced the rate of tumor growth approximately 250% (p<0.0002).

EXAMPLE 3

In vitro Evaluation of Sphingomyelin Therapy on Colonic Tumors

Sphingomyelin enhancement of chemotherapy was evaluated by measuring its effect on 5-fluorouracil or doxorubicin (DOX) treatment of colonic tumors grown in culture. Cell viability was measured using the dye MTT (3-(4,5-dimethylthiazol-2-yl)-2,5-diphenyl tetrazolium bromide) in a 24-well chamber format. See Mosmann, T., *J. Immunol. Methods*, 65:55–63 (1983). HCT15, HT29, LoVo, LS174T, MOSER, SW480 and WiDr human colonic tumor cells were maintained in RPMI media supplemented with 10% fetal calf serum. Human umbilical cord venous endothelial cells (HUVEC) from pooled donors (Clonetics/BioWhittaker, San Diego, Calif.) were used as controls. Cells ($10^4$/well) were plated in the presence of varying concentrations of drug and sphingomyelin and grown in a humidified incubator. As an additional control, egg yolk phosphatidylcholine (PC) (Sigma, St. Louis, Mo.) was added to the cells instead of sphingomyelin. Drugs and lipids were added to HUVEC cells 24 hours after plating, but otherwise were treated the same. After four days, the media was replaced with media containing 0.5 mg/ml MTT and incubated two to four hours at 37° C. An equal volume of 0.04 N HCl in isopropanol was added, and the absorbance at 570 nm was measured. The $IC_{50}$ values, defined as the concentration of drug necessary to reduce cell viability by 50%, from three to seven independent experiments were averaged and compared using ANOVA.

Figure 3:
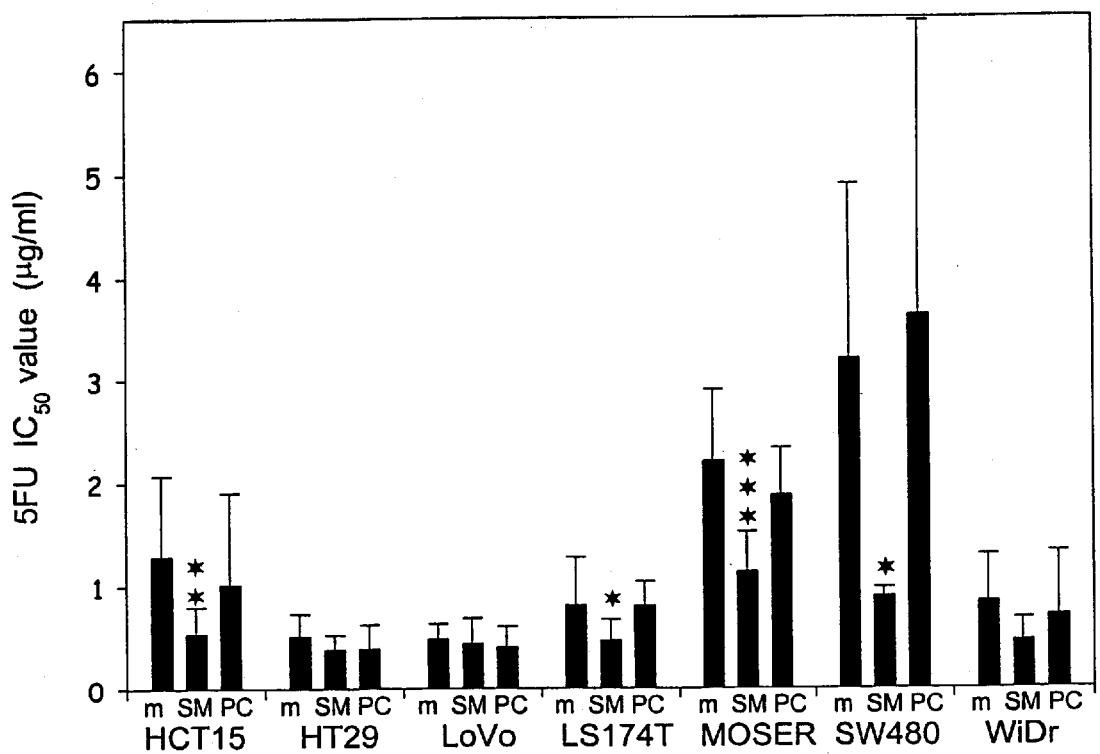
FIG. 3 demonstrates that sphingomyelin alters 5FU chemosensitivity of tumor cell lines in vitro. The $IC_{50}$ values are graphed with standard deviations. The following symbols are used: m, media (no lipid); SM, sphingomyelin; PC, phosphatidylcholine. Three to six independent experiments were compiled and compared by ANOVA: *, $p<0.1$; , $p<0.05$; *, $p<0.01$; **** $p<0.005$.
Figure 4:
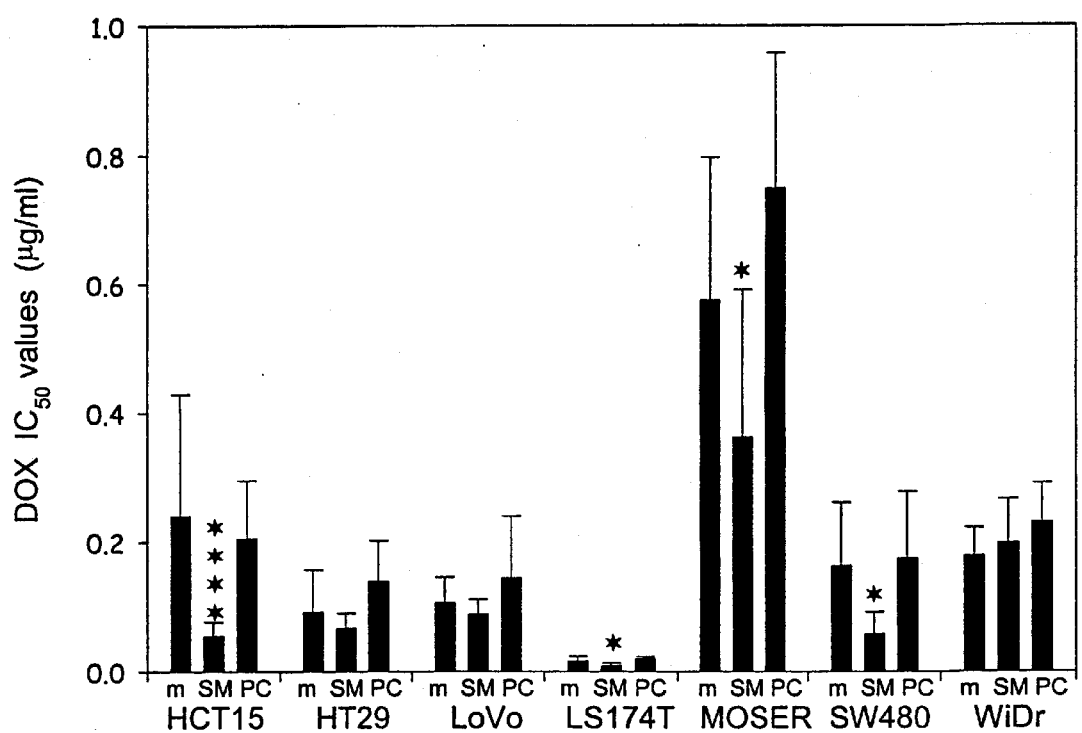
FIG. 4 demonstrates that sphingomyelin alters DOX chemosensitivity of tumor cell lines in vitro. The $IC_{50}$ values are graphed with standard deviations. The following symbols are used: m, media (no lipid); SM, sphingomyelin; PC, phosphatidylcholine. Three to six independent experiments were compiled and compared by ANOVA: *, $p<0.1$;  $p<0.05$; * $p<0.01$; ****, $p<0.005$.

The results are depicted graphically in FIGS. 3 and 4. In the presence of 1 mg/ml SM, HT29 cells displayed nearly the same $IC_{50}$ for 5FU (0.52±0.21 μg/ml, media; 0.38±0.15 μg/ml, SM; 0.39±0.24 μg/ml, PC) and DOX (92±64 ng/ml, media; 67±23 ng/ml, SM; 139±63 ng/ml, PC). Sphingomyelin sensitized the other six cell lines to both 5FU and DOX to varying degrees (See FIGS. 3 and 4). Sphingomyelin increased 5FU and DOX sensitivity in HCT15 (140% and 340%, respectively), LS174T (70% and 70%, respectively), MOSER (90% and 100%, respectively) and SW480 cells (260% and 180%, respectively). The cell lines HT29, LoVo and WiDr were not chemosensitized by sphingomyelin in vitro. Similarly, sphingomyelin did not sensitize HUVEC cells to 5FU or DOX therapy (data not shown). The enhancement of chemosensitivity appears to be a function of the ceramide portion of sphingomyelin, since PC does not elicit a similar effect as sphingomyelin. The differences between the in vivo and in vitro results may be due to the environment in which tumor cells grow.

What is claimed is:

1. A method of treatment comprising administering a cytotoxic tumor therapy to a patient, and a therapeutically effective amount of sphingomyelin as an adjunct to said cytotoxic tumor therapy, wherein said therapeutically effective amount of sphingomyelin enhances the cytotoxicity of said cytotoxic tumor therapy.

2. The method of claim 1, wherein said tumor therapy comprises chemotherapy.

3. The method of claim 2, wherein said chemotherapy is targeted to tumor cells using an antibody or an antibody fragment.

4. The method of claim 3, wherein said antibody or antibody fragment is a monoclonal antibody or a fragment of a monoclonal antibody.

5. The method of claim 1, wherein said therapeutically effective amount of sphingomyelin is an amount of at least about 10 mg/day.

6. The method of claim 2, wherein said chemotherapy comprises administering 5-fluorouracil.

7. The method of claim 2, wherein said chemotherapy comprises administering doxorubicin.

8. The method of claim 1, wherein said sphingomyelin is administered orally.

9. The method of claim 1, wherein said sphingomyelin is administered parenterally.

10. The method of claim 1, wherein said sphingomyelin is administered prior to administration of said tumor therapy.

* * * * *